United States Patent [19]
Takama et al.

[11] Patent Number: 6,043,034
[45] Date of Patent: Mar. 28, 2000

[54] METHOD FOR MEASURING THE CONCENTRATION OF POLYNUCLEOTIDES

[75] Inventors: Toshio Takama, Nara; Yung Xiang Wang, Shiga; Masao Kono; Xiaoming Dou, both of Osaka, all of Japan

[73] Assignee: Kyoto Daiichi Kagaku Co., Ltd., Kyoto, Japan

[21] Appl. No.: 08/955,251

[22] Filed: Oct. 21, 1997

[30] Foreign Application Priority Data

Oct. 25, 1996 [JP] Japan .................................. 8-284153

[51] Int. Cl.⁷ .............................. C12Q 1/68; C07H 21/02; C07H 21/04; C12N 15/00
[52] U.S. Cl. ........................... 435/6; 536/23.1; 536/24.3; 935/76; 935/77; 935/78
[58] Field of Search ............................ 435/6; 536/23.1, 536/24.3; 935/76, 77, 78

[56] References Cited

U.S. PATENT DOCUMENTS

| | | | |
|---|---|---|---|
| 4,775,636 | 10/1988 | Moeremans et al. ................... | 436/518 |
| 4,781,458 | 11/1988 | Angel et al. ........................... | 356/301 |
| 5,266,498 | 11/1993 | Tarcha et al. .......................... | 436/525 |
| 5,341,215 | 8/1994 | Seher ..................................... | 356/445 |
| 5,376,556 | 12/1994 | Tarcha et al. .......................... | 436/525 |
| 5,814,516 | 9/1998 | Vo-Dinh .............................. | 435/272.2 |
| 5,864,397 | 1/1999 | Vo-Dinh ................................ | 356/301 |
| 5,866,430 | 2/1999 | Grow ..................................... | 436/172 |
| 5,869,255 | 2/1999 | Mathies et al. ............................ | 435/6 |
| 5,882,863 | 3/1999 | Imai et al. ................................ | 435/6 |

FOREIGN PATENT DOCUMENTS

| | | |
|---|---|---|
| 0 587 008 | 3/1994 | European Pat. Off. . |
| 0587008A1 | 3/1994 | European Pat. Off. . |
| WO 90/02205 | 3/1990 | WIPO . |
| WO 97/05280 | 2/1997 | WIPO . |

OTHER PUBLICATIONS

Communication from European Patent Office and attached Search Report (Application No. 97308444.5–2116–), Feb. 1998.

F. Zimmermann et al., "SERRS Study of Acridine Orange and Its Binding to DNA Strands" *J. Phys. Chem.*, vol. 98, pp. 12796–12804, 1994.

C.H. Munro et al., "Qualitative and Semi–quantitative Trace Analysis of Acidic Monoazo Dyes by Surface Enhanced Resonance Raman Scattering" *Analyst*, vol. 120, pp. 993–1003, Apr. 1995.

Therese M. Cottom et al., "Application of Surface–Enhanced Raman Spectroscopy to Biological Systems" *Journal of Raman Spectroscopy*, vol. 22, pp. 729–742, 1996.

Communication from European Patent Office and attached Search Report (Application No. 97308491.6–2116–), Feb. 1998.

A. Helmenstine et al., "Measurement of DNA Adducts Using Surface–Enhanced Raman Spectroscopy" *Journal of Toxicology and Environmental Health*, pp. 195–202, 1993.

K. Kneipp et al., "Surface Enhanced Raman Scattering (SERS) of Nucleic Acids Adsorbed on Colloidal Silver Particles" *Journal of Molecular Structure*, pp. 173–179, 1986.

T. Vo–Dinh et al., "Surface–Enhanced Raman Gene Probes" *Anal. Chem.*, vol. 66, No. 20, pp. 3379–3383.

(List continued on next page.)

*Primary Examiner*—W. Gary Jones
*Assistant Examiner*—Ethan Whisenaut
*Attorney, Agent, or Firm*—Merchant & Gould P.C.

[57] ABSTRACT

A method for measuring the concentration of polynucleotide in a sample comprising the steps of: (1) preparing a sample, a Raman scattering active agent capable of bonding to a polynucleotide and a surface-enhanced Raman scattering (SERS) active substrate capable of capturing the agent; (2) mixing the sample, the agent and the substrate to capture the agent which has not been bonded to polynucleotide on the surface of the substrate; (3) irradiating the mixture; and (4) measuring the SERS radiation which is generated by the agent captured on the surface of the substrate.

11 Claims, 8 Drawing Sheets

OTHER PUBLICATIONS

G. Terrance Walker et al., "Strand Displacement Amplification—an Isothermal, in vitro DNA Amplification Technique", *Nucleic Acids Research*, vol., 20, No. 7, pp. 1691–1696, 1992.

Takahiko Ishiguro, "IM–PCR (Intercalation Monitoring PCR)", *Progress in Medical,* vol. 173, No. 12, pp. 959–963. (English translation of p. 959, col. 1, lines 1–4 and Figure 1—Homogeneous PCR Assay).

Bej et al, "Amplification of nucleic acids by polymerase chain reaction and other methods and their applications", Critical Reviews in Biochem. Mol. Biol. 26(3/4)301–334 (1991).

Stratagene catalog, p. 39 (1988).

Graham et al, "Selective detection of deoxyribonucleic acid at ultralow concentration by SERRS", Anal. Chem. 69:4703–4707 (Nov. 1997).

METHOD FOR MEASURING THE CONCENTRATION OF POLYNUCLEOTIDES

FIELD OF THE INVENTION

The present invention relates to a method for measuring the concentration of polynucleotide such as deoxyribonucleic acid (DNA) or ribonucleic acid (RNA) in a sample using surface-enhanced Raman scattering (SERS) and to a kit for use in such a method.

BACKGROUND OF THE INVENTION

Recent innovation in the field of genetic engineering has been remarkable. In particular, the development of a polymerase chain reaction (PCR) method has enabled the mass replication of target DNA. The PCR method is based on the principle that DNA polymerase does not function without a primer. The PCR method is used to amplify DNA in large amounts by repeating the following cycle: (1) DNA in a sample is heat denaturated resulting in single stranded DNA, (2) a primer is bonded to the DNA under reduced temperature and (3) the DNA is formed by thermo-stable DNA polymerase under this condition. Consequently, target DNA can be prepared in large amounts by using a specific primer prepared by chemical synthesis or otherwise. In this method, the replication of target DNA is typically monitored by electrophoresis.

OBJECTS OF THE INVENTION

However, electrophoresis is a complex and lengthy technique in which it is necessary to prepare a gel as a carrier and to pre-select a gel (size) for which PCR was carried out with regard to the size of DNA. Typically, a sample takes about 75 minutes to electrophorese and it is therefore not a rapid technique. The invention seeks to solve these problems and others in the known techniques for measuring polynucleotide concentration in a sample.

It is an object of the present invention to provide a method which makes it possible to measure the concentration of polynucleotide in a sample easily and in a short timescale. It is a further object of the invention to provide a kit for such a use.

SUMMARY OF THE INVENTION

Thus viewed from one aspect the present invention provides a method for measuring the presence of polynucleotide in a sample comprising the steps of (1) preparing a sample, a Raman scattering active agent capable of bonding to a polynucleotide and a surface-enhanced Raman scattering (SERS) active substrate capable of capturing said agent; (2) mixing said sample, said agent and said substrate to capture said agent which has not been bonded to polynucleotide on the surface of said substrate; (3) irradiating said mixture; and (4) measuring SERS radiation which is generated by said agent captured on the surface of said substrate. Preferably the method is used to determine the concentration of said polynucleotide.

There are many known Raman scattering active agents. One particular agent which may be used in the present invention bonds to polynucleotide specifically and when it is added to the sample it will bond to any polynucleotide present in the sample. Any agent not bonded to polynucleotide is captured on the surface of the SERS active substrate. If the sample is irradiated, only the agent captured on the SERS active substrate generates SERS radiation, whilst the agent bonded to the polynucleotide generates no SERS radiation. Thus, the detected SERS radiation is inversely proportional to the concentration of polynucleotide in the sample, thereby allowing the concentration of the polynucleotide to be determined.

The agent and the substrate may be added at the same time or consecutively, e.g. the agent may be added before the substrate.

The method according to the invention is easy to carry out, since it comprises simple steps, i.e. preparing, mixing, irradiating and measuring. Moreover, the steps according to the method of the present invention may be carried out in a short timescale, since the bonding of the agent to polynucleotide, the capture of the agent on the surface of the substrate occur is rapid and the SERS radiation can be measured over a short period, e.g. of about 1–2 seconds.

In the present invention, the term "Raman activity" refers to Raman scattering or SERS generated by irradiation, and the term "the Raman scattering active agent which bonds to polynucleotide" refers to the agent capable of bonding to polynucleotide and exhibiting Raman activity. Further, "SERS active substrate" is a substrate capable of enhancing Raman scattering by capturing the agent on its surface. The agent may be captured by adsorption, by electrical adsorption (by supplying electric potential), or by reacting and bonding with a functional group on the substrate.

The polynucleotide under investigation may be, for example, single stranded DNA, double stranded DNA, RNA, or a complex of RNA and DNA. The method of the present invention is effective on a sample which has been subjected to the PCR method (PCR product) or on a DNA sample. As mentioned above, the PCR method is used for amplifying target DNA. If target DNA is not present in the sample, trace amounts of DNA would be found in the PCR product. Therefore, by measuring the SERS radiation in accordance with the method of the present invention, it may be determined simply and rapidly whether or not the target DNA has been amplified. Further, the amount of amplified DNA can be measured provided a calibration curve has been prepared beforehand.

In addition, the method of the present invention may usefully be applied to samples in which the amplification of DNA is carried out by the Strand displacement amplification method (SDA method) or by the Ligase chain reaction (LCR method) and in which the amplification of RNA is carried out using the Qβ replicas (Qβ method). The SDA method includes the method described in Nucleic Acids Research, Vol.20. No.7 1691–1696. The LCR method is that method in which thermo-stable DNA ligase which is not denaturated by heat (even at 94° C.) is used. This method is based on the principle that for normal DNA samples having no mismatches, the two kinds of oligonucleotide used are bonded by the DNA ligase, resulting in them functioning as a substrate in the next reaction cycle and DNA amplification. Where the DNA sample has mismatches, the reaction stops, since the two kinds of oligonucleotide are not able to bond.

A RNA replicas which has high specificity to substrate RNA is used in the Qβ method. Firstly, the plasmid vector connected to MDV-1-RNA (RNA changing to DNA) is placed downstream of the promoter of T7 RNA polymerase and the DNA fragment to be amplified is inserted into the MDV-1 (the fragment of about 20–800 bp can be inserted into it). After it is cut by using a restriction enzyme, the DNA fragment is charged to RNA by using T7 RNA polymerase. The MDV-1-RNA in which the DNA fragment is inserted can be amplified by repeating the replicative cycle with Qβ replicas.

In addition, the method of the present invention may usefully be applied to samples in which the amplification of DNA or RNA is carried out by a 3SR method, a NASBA method, a CPR method, a SIR method or the like. The NASBA method is an RNA replication method and the other methods are DNA replication methods.

For measuring the concentration of double stranded DNA (including a sample treated by a DNA replication method) in accordance with the invention, the agent may be 4', 6-diamidino-2- phenylindole (DAPI) which is shown in formula 1 below, ethidium bromide (EtBr), thiazole orange, bisbenzimide (Hoechst 33258, product of Hoechst AG) which is shown in formula 2 below and acridine orange. In addition, SYBR Green I (Molecular Probes Co., Ltd.) may be included. It is preferable that the chosen agent is DAPI, since it bonds to double stranded DNA to form a complex but barely bonds to other material such as RNA. Therefore, double stranded DNA can be selectively detected by DAPI.

<Formula 1>

<Formula 2>

For measuring the concentration of RNA in accordance with the invention, the agent may include, e.g. EtBr, thiazole orange, bisbenzimide (Hoechst 33258, product of Hoechst AG) which is shown in formula 2 and acridine orange. Additionally, SYBR Green II (Molecular Probes Co., Ltd.) may be included. Among the materials mentioned above, SYBR Green II bonds to RNA more selectively to form a complex.

For measuring the concentration of single stranded DNA in accordance with the invention SYBR Green II may be used as the agent.

For measuring the concentration of a complex of RNA and DNA an agent which bonds to DNA and/or RNA may be used as the agent.

In the present invention, the SERS active substrate may be, for example, a silver colloid, a gold colloid, a copper colloid, an electrode or a metal plate, preferably a metal colloid such as silver colloid and gold colloid which may be simply manufactured and easily treated.

The kit of the present invention comprises a reagent R1 having the agent and a reagent R2 having the substrate. The measurement of the concentration of polynucleotide in the present invention can be carried out more rapidly and easily by using this kit.

DETAILED DESCRIPTION OF THE INVENTION

FIG. 1 shows an example in which the present invention was applied to a sample upon which PCR had been carried out. In the example on the right side, PCR had been carried out for samples in which target DNA was not present (i.e. non-target DNA (1)), and on the left side, PCR had been carried out for samples in which target DNA (2) was present.

Figure 1A:
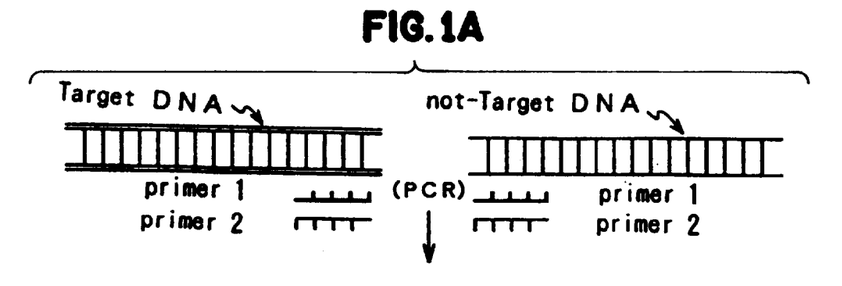
FIG. 1 shows schematically a series of manipulations of one embodiment of the invention in which the method was applied to the PCR.
Figure 1B:
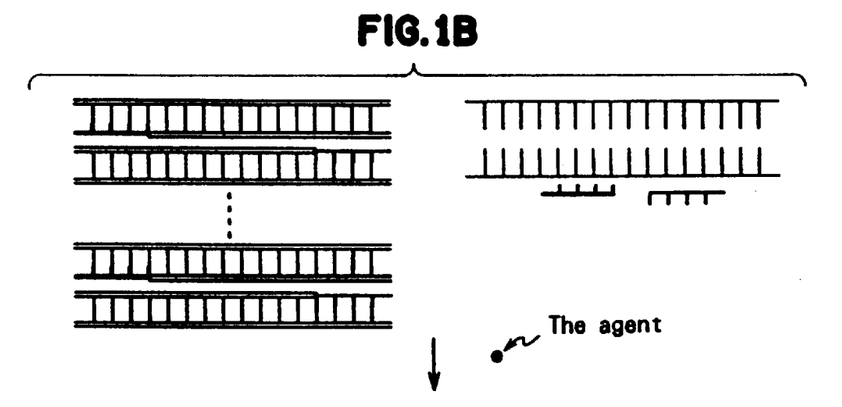

As shown in FIG. 1(a) a DNA sample was initially prepared. Primers (3) and (4), DNA polymerase (not shown in this Figure) and deoxyribonucleotidetriphosphate (dNTP, not shown in this Figure) were added to the sample. When the sample was heated, DNA was denaturated and dissociated to single stranded DNA. On cooling, the primers were bonded to the target DNA complementally, but not to the other DNA. As shown in FIG. (b), extension occurred in the target DNA by the DNA polymerase. However, it did not occur in the DNA to which primers did not bond. When a series of manipulations were repeated about 20–30 times, the target DNA was amplified in large amounts as shown in FIG. (b). The other DNA was not amplified at all.

Figure 1C:
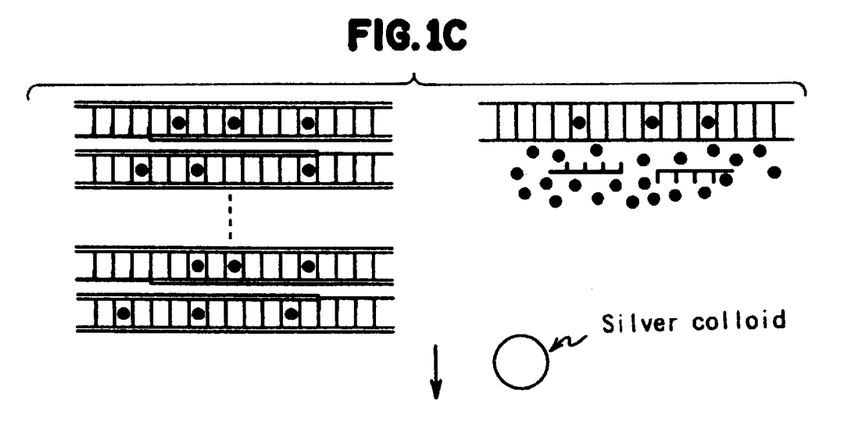
Figure 1D:
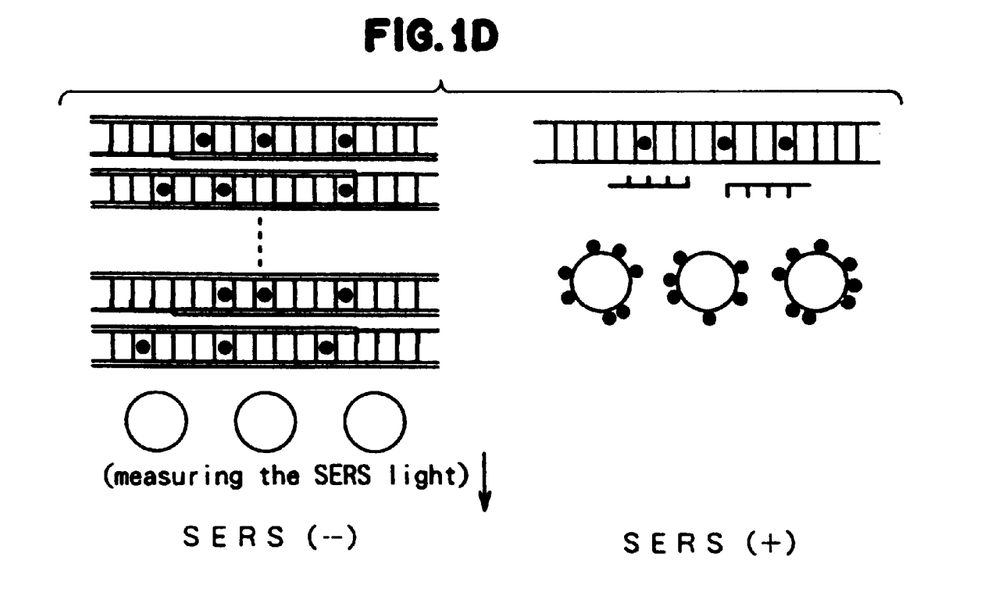

As shown in FIG. (c), when the agent (5) which bonded to polynucleotide was added to the samples, it intercalated into the double stranded DNA. Consequently, there was a lot of double stranded DNA in the target DNA sample as shown in the Figure, and almost all of the agents were bonded to the double stranded DNA. On the contrary, in the sample not comprising the target DNA, the greater part of the agent was present in the sample in free state, since there was almost no double stranded DNA. A silver colloid (SERS active substrate) (6) was added to the samples as shown in FIG. (d). As a result, no agent was captured by the silver colloid (even if there was any, it can be ignored as trace amount), since the agent was bonded to the DNA in the target DNA sample as shown in the Figure. However, the silver colloid captured the agent which was present in flee state in the sample.

Under this condition, when the sample was irradiated, SERS radiation was faintly observed or not observed in the target DNA sample. On the other hand, strong SERS radiation was observed in the sample not comprising target DNA. In other words, the results indicated that target DNA was not present in the sample and that target DNA was present in the sample in which SERS radiation was faintly observed or not observed.

Thus, according to the present invention, measuring the concentration of polynucleotide is possible in a short timescale without complicated manipulations such as gel and buffer solution preparation in electrophoresis.

Irradiation and conventional measurement of SERS radiation may be carried out using conventional Raman scattering measurement apparatus. The conditions of the measurement are determined by the type and dosage of agent used, the concentration of the polynucleotide, etc. The intensity of the argon ion laser is generally in the range 5 mW–100 mW. In the present invention, it is preferable that the SERS active substrate is added to the sample in excess of the agent.

In the present invention, it is preferable that the weight ratio between the polynucleotide and the agent is determined beforehand, so that the SERS radiation intensity in cases where the target DNA is present and the intensity in cases where the target DNA is not present can be clearly distinguished. The weight ratio is determined by the characteristics of the polynucleotide and the agent. For example, when the polynucleotide is double stranded DNA and the agent is DAPI, the weight ratio is generally DNA/DAPI=0.1–0.5.

The kit according to the present invention comprises a reagent Rn1 comprising a Raman scattering active agent capable of bonding to polynucleotide and a reagent R2 comprising SERS active substrate capable of capturing the agent.

The reagent R1 may include components other than the agent. The reagent R2 may also include, for example, stabilizers such as polyphosphoric acid, polyvinyl alcohol (PVA), polyvinyl-pyrrolidone (PVP), surfactant and the like.

The kit according to the invention enables the measurement of the concentration of polynucleotide to be carried out rapidly and easily, since the proper amount of the necessary components have been prepared and thus it is not necessary to prepare the reagents each time the measurement is carried out as in the conventional method.

In the above description, the polynucleotide is double stranded DNA which has been amplified by PCR. However, the present invention should not be limited to the example. The present invention may be equally applied to double stranded DNA amplified by the SDA method or by the LCR method, to RNA, to RNA amplified by the Qβ method, to single stranded DNA or to a complex of RNA and DNA. The same steps as mentioned above may be carried out with an agent suitably selected according to the kind of polynucleotide under investigation.

The following Examples are intended to illustrate the invention in a non-limiting manner:

EMBODIMENT

EXAMPLE A

First, a PCR buffer was prepared by dissolving the reagents shown below into purified water (1l).

| (The PCR Buffer Composition) | |
|---|---|
| Tris-HCl (pH 8.3) | 100 mM |
| KCl | 500 mM |
| MgCl$_2$ | 15 mM |

The PCR reaction solution was prepared by adding the materials shown below to 10 μl of the PCR buffer. The primers 1 and 2 shown below have the complementary sequence to the following λ DNA.

```
(Mixed materials)
    dNTP (dATP, dCTP, dGTP, dTTP, 2.5mM): 8 μl
    primer 1 (20 pmol/μl): 1 μl
            Sequence: 5'-GATGAGTTCGTGTCCGTACAACT-3'
    primer 2 (20 pmol/μl): 1 μl
            Sequence: 5'-CCACATCCATACCGGGTTTCAC-3'
    TaqDNA polymerase (50U/μl): 0.5 μl
    DNA (λ DNA, 1 μg/ml): 1 μl
    distilled water: 78.5 μl
```

Using this PCR reaction solution, PCR was carried out by the following cycle.
(PCR Cycle)
 Step a (94° C., 10 minutes):1 cycle
 Step b (94° C., 1 minute)→Step c (68° C., 4 minutes):30 cycles
 Step d (68° C., 7 minutes):1 cycle DNA purification was carried out, i.e. first, the PCR product was electrophoresed using an agarose-gel (150 mA, 2 hours) whereby the target DNA fraction was separated out. The gel portion having the band of the target DNA was cut and ejected. The gel was put into a dialysis tube with the TBE buffer and both ends of the tube were closed with sealers. The dialysis tube was installed in the electrophoresis bath so that the major axis of the dialysis tube was at right angles to the direction of the electric field. The bath was filled with TBE buffer and energized (150 mA, 3 hours). After energizing, the TBE buffer recovered fiom the dialysis tube was transferred to a centrifuging tube and precipitation was carried out with ethanol. The precipitate was dissolved in distilled water. The solution was purified DNA sample.

Next, 15 μl DAPI aqueous solution (concentration:10⁻⁴mol/l) was mixed with 25 μl of the DNA sample. 360 μl silver colloid aqueous solution (concentration: 0.17 mg/ml) was mixed with the mixture solution to prepare the test sample. In the test sample, the SERS radiation was measured using an argon ion laser (nlaser intensity:50 mW) with 514.5 nm excitation wavelength and 5 seconds exposure time. The result is shown in curve (a) of FIG. 2.

Figure 2:
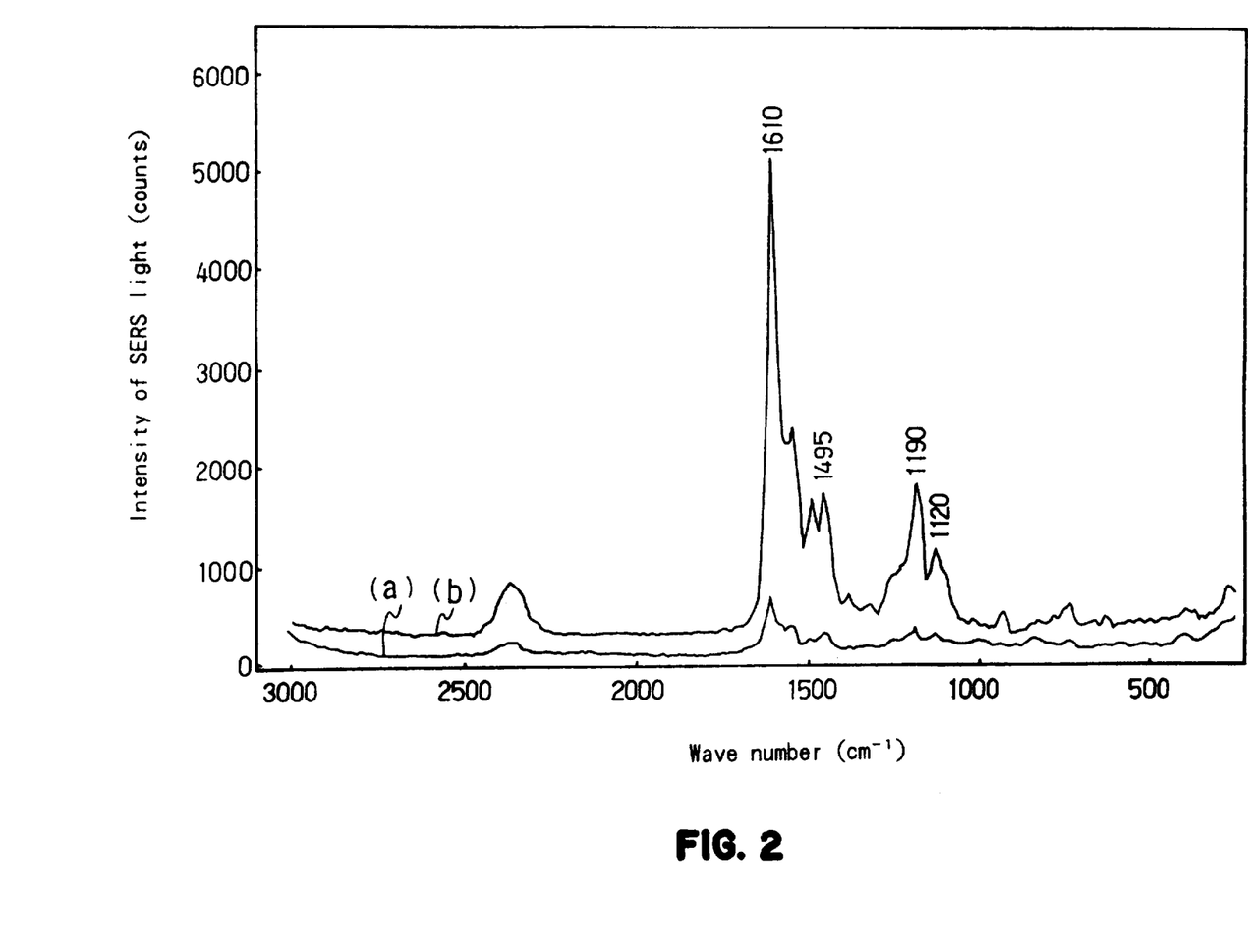
FIG. 2 shows a graph of SERS radiation of one embodiment of the present invention.

In FIG. 2, the vertical axis in the graph shows the intensity of the SERS radiation and the horizontal axis shows the wave number of the SERS radiation. FIGS. 3, 4, 5 and 7 are presented in the same manner.

Comparative Example 1

PCR was carried out and the SERS radiation was measured in the same manner as in Example A but using 1 μl distilled water instead of DNA solution. The result is shown in curve (b) of FIG. 2.
(Control 1 and 2)

Control 1: the example using 40 μl DAPI aqueous solution (concentration:$10^{-5}$ mol/l) instead of the mixture solution.

Control 2: the example measuring SERS radiation of 40 μl double stranded DNA aqueous solution without DAPI and silver colloid.

Figure 4:
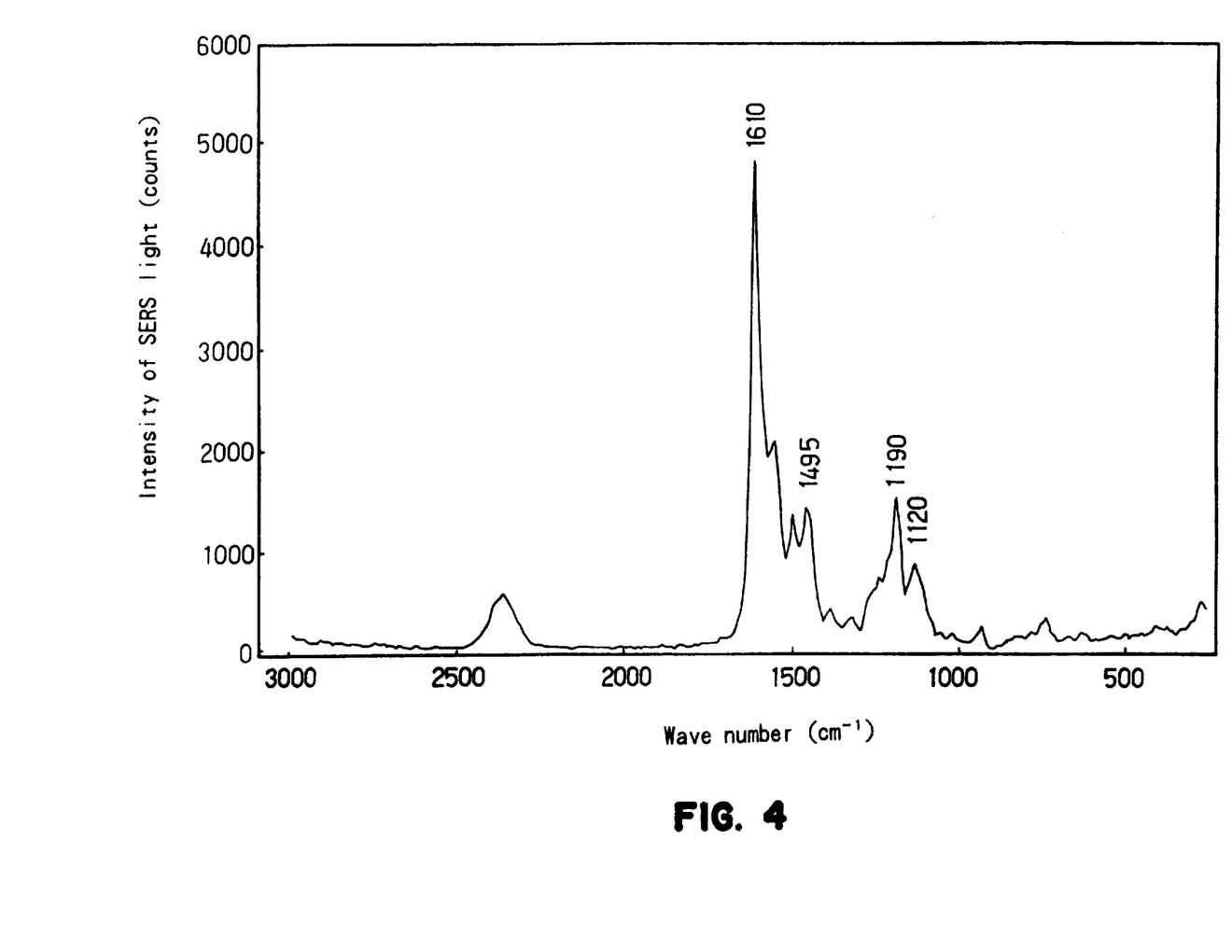
FIG. 4 shows a graph of SERS radiation in the case of using only DAPI.

The other conditions and manipulations of Control 1 and 2 were identical to Example A. The result of Control 1 is shown in FIG. 4 and the result of Control 2 in FIG. 5.

Figure 5:
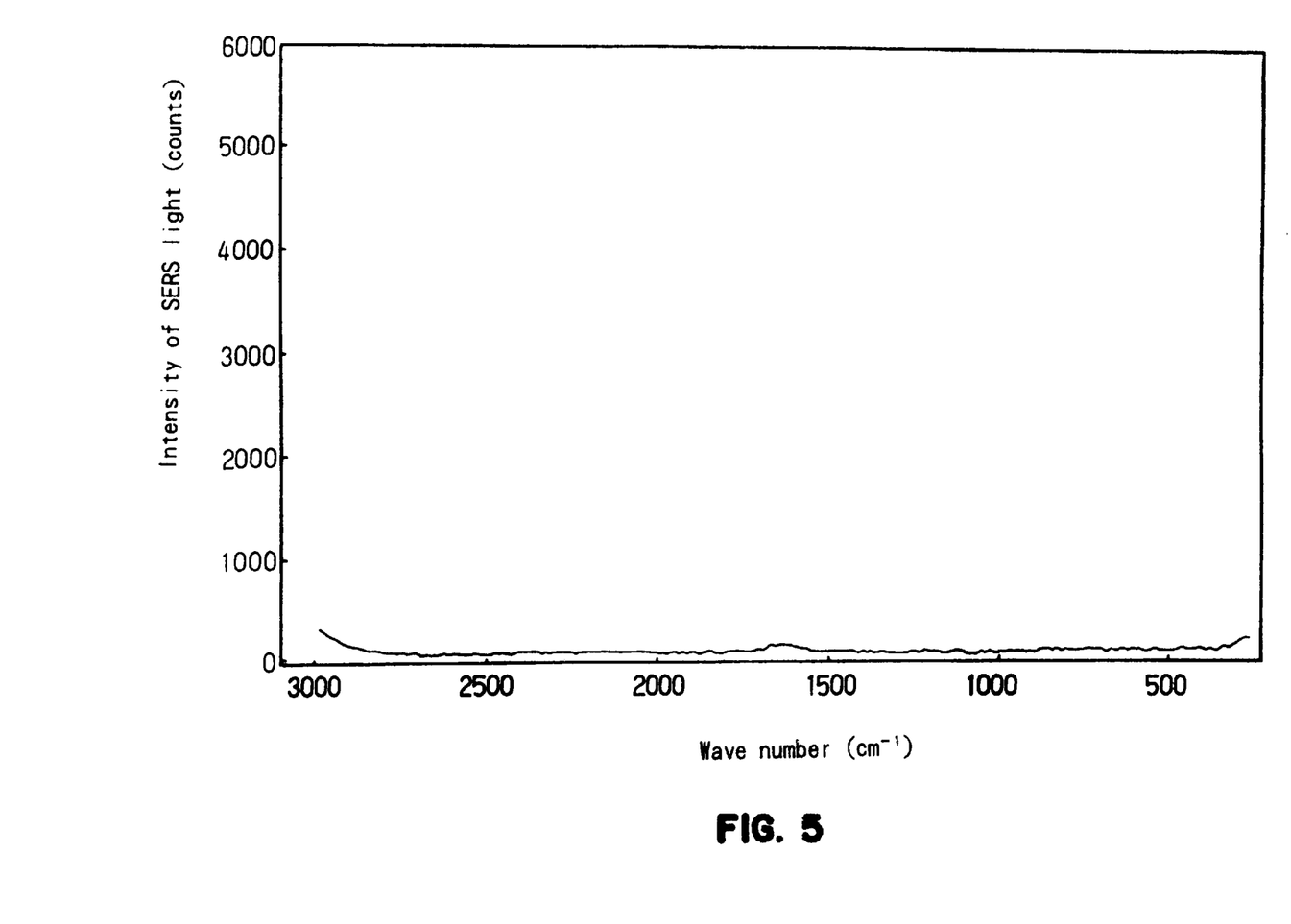
FIG. 5 shows a graph of SERS radiation in the case of using only DNA.

According to the results of Example A, Comparative Example 1, Control 1 and 2, it can be said that: as shown in curve (a) of FIG. 2, in Example A in which DNA was amplified by PCR, the SERS radiation was slightly measured, since almost all DAPI was intercalated into the DNA, thereby only trace amounts of DAPI were captured by the silver colloid. On the other hand, as shown in curve (b) in FIG. 2, in Comparative Example 1 in which DNA was not amplified by PCR, strong SERS radiation was measured, since almost all DAPI was captured by the silver colloid. Furthermore, the peak of SERS radiation in Comparative Example 1 conformed with that in Control 1 shown in FIG. 4. Additionally as shown in FIG. 5, SERS radiation was not measured in Control 2. According to these results, it may be said that the presence of target DNA in the sample was judged easily and rapidly by using the method of the invention.

EXAMPLE B

PCR was carried out in the same manner as in Example A and the PCR product was purified. 5 μl DAPI aqueous solution (concentration: $10^{-4}$ mol/l) was mixed with 35 μl of the purified DNA sample. 360 μl silver colloid aqueous solution (concentration: 0.17 mg/ml) was mixed with the mixture solution to prepare the test sample. In the test sample, the SERS radiation was measured using an argon ion laser nGaser intensity: 50 mW) with 514.5 nm excitation wavelength and 5 seconds exposure time. The result is shown in curve (a) of FIG. 3.

Comparative Example 2

PCR and DNA purification were carried out and SERS radiation was measured in the same manner as in Example B but using 1 μl distilled water instead of DNA solution. The result is shown in curve (b) of FIG. 3.

Figure 3:
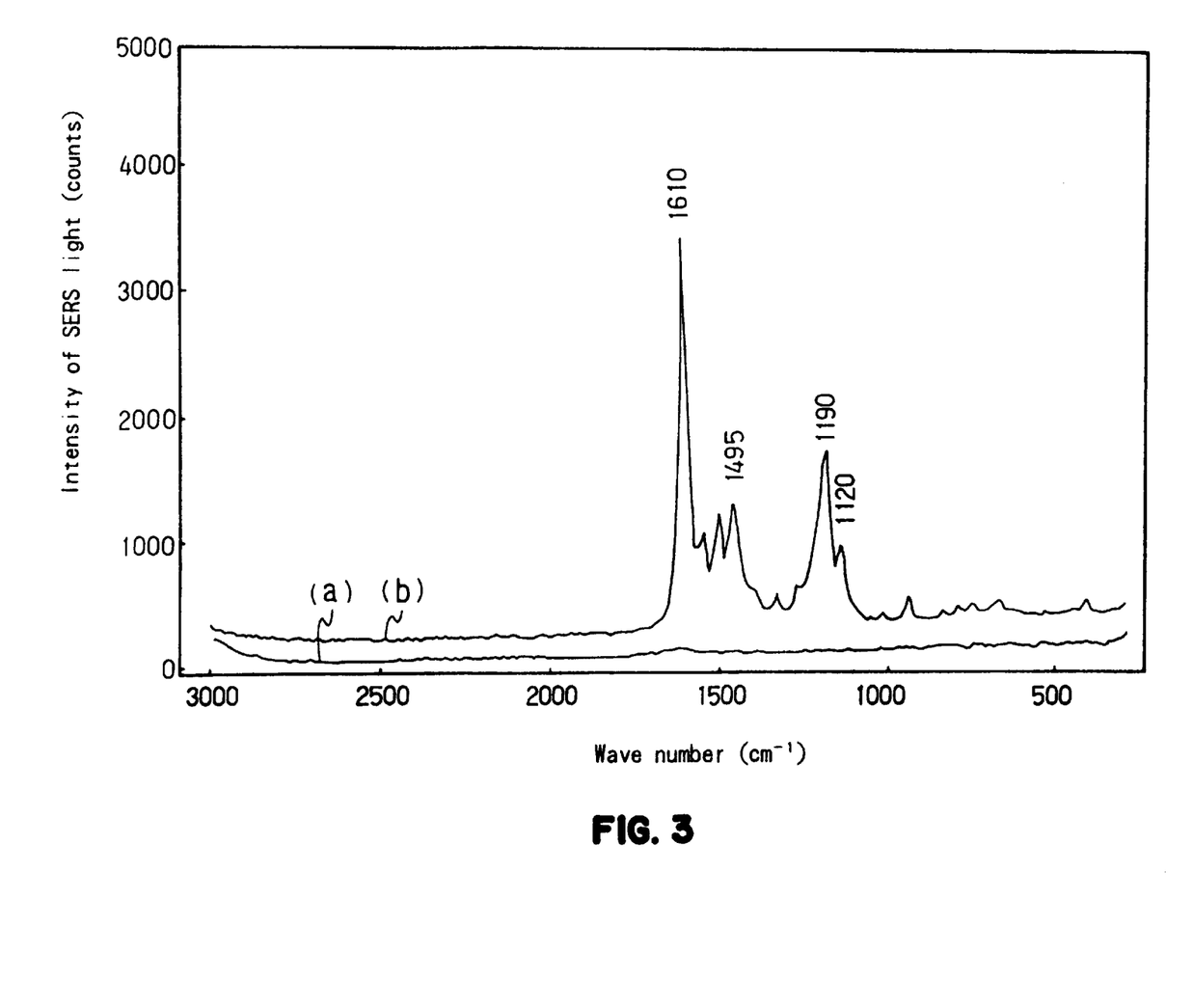
FIG. 3 shows a graph of SERS radiation of one embodiment of the present invention.

According to the results of Example B and Comparative Example 2, it can be said that as shown in curve (a) of FIG. 3, in Example B (in which DNA was amplified by PCR) SERS radiation was not detected, since DAPI was almost completely intercalated into DNA and was not captured by the silver colloid. On the other hand, as shown in curve (b) of FIG. 3, in Comparative Example 2 in which DNA was not amplified by PCR, strong SERS radiation was measured, since almost all DAPI was captured by the silver colloid.

EXAMPLE C

Figure 6:
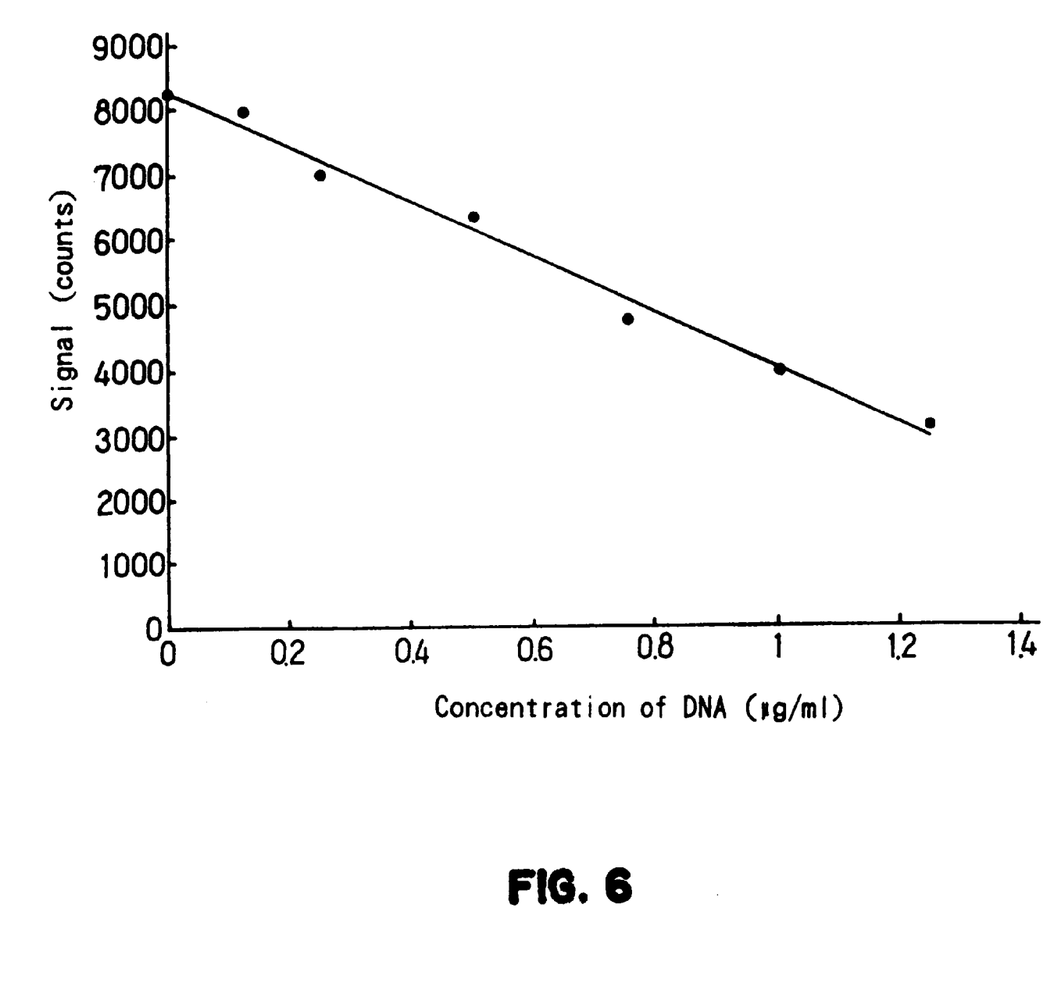
FIG. 6 is a graph showing the relationship between SERS radiation and DNA concentration in another embodiment of the present invention.

SERS radiation was measured in the same manner as in Example A but using the following mixture solution as a test sample. The mixture solution was prepared by mixing 15 μl DAPI aqueous solution with 25 μl DNA aqueous solutions having various DNA concentrations. The result is shown in FIG. 6. In this Figure, the vertical axis shows the intensity of SERS radiation and the horizontal axis shows DNA concentration.

As shown in FIG. 6, the intensity of SERS radiation decreased linearly as the DNA concentration increased. This graph which can be used as a calibration curve enables, for example, not only the determination of the presence of target DNA in the sample treated by PCR, but also the measurement of DNA concentration in the PCR product.

EXAMPLE D

In Example D, the same manipulations as in Example A were carried out under the same conditions as in Example A without DNA purification. The result is shown in curve (a) of FIG. 7.

In Comparative Example 2, the same manipulations as Example A were carried out under the same conditions as in Comparative Example 1 without DNA purification. The result is shown in curve (b) of FIG. 7.

Figure 7:
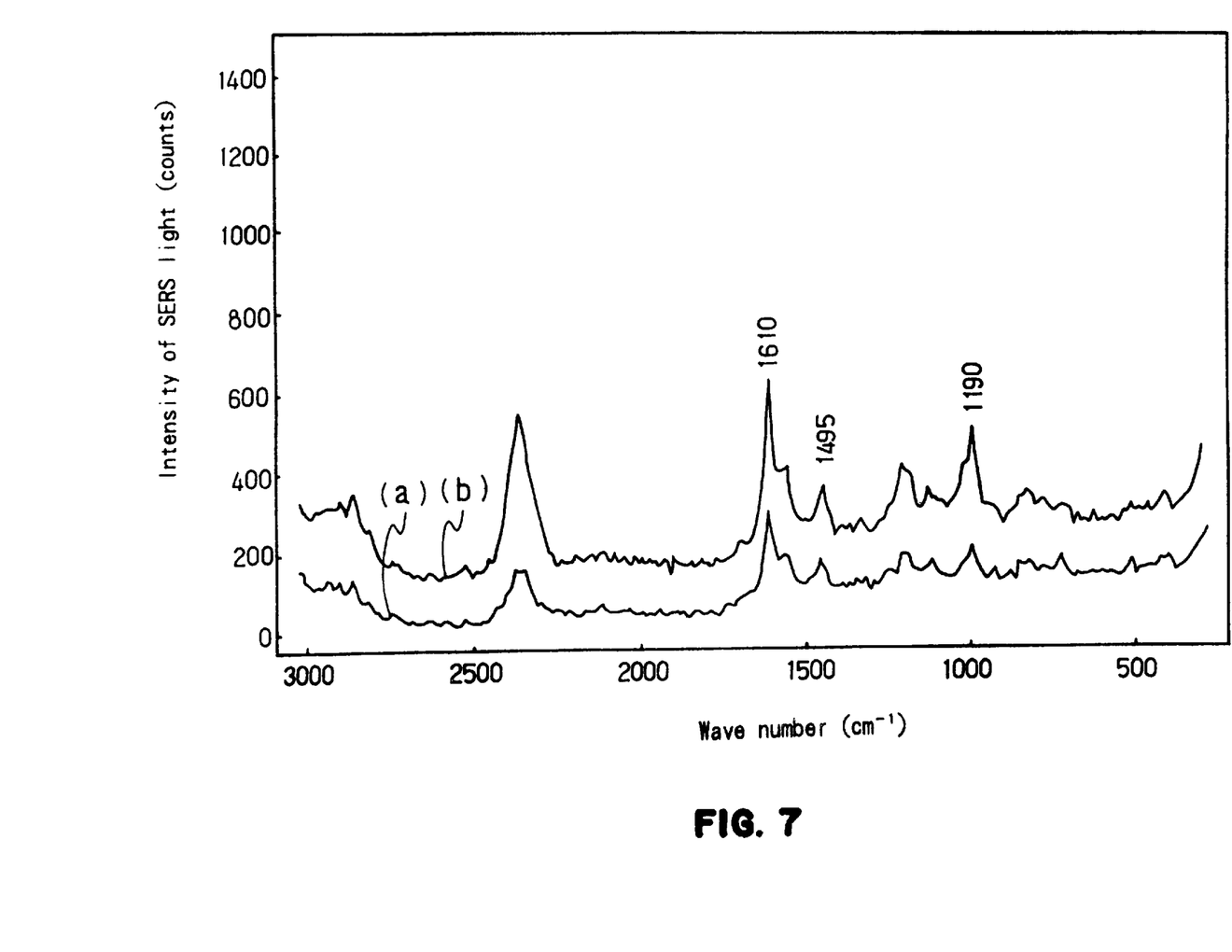
FIG. 7 shows a graph of SERS radiation in another embodiment of the present invention.

As shown in FIG. 7, the SERS radiation in Example D in which DNA is present in large amounts can be distinguished clearly from the SERS radiation in Comparative Example 2 in which almost no DNA is present. From this result, the method of the present invention enables the concentration of polynucleotide in PCR products in which the purification of DNA was not carried out to be measured.

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. A method for measuring the presence of polynucleotide in a sample, comprising the steps of:

preparing a sample, a Raman scattering active agent capable of bonding to a polynucleotide and a surface-enhanced Raman scattering (SERS) active substrate capable of capturing said agent;

mixing said sample, said agent and said substrate, whereby the surface of the substrate captures Raman scattering active agent that has not been bonded to polynucleotide in the sample;

irradiating said mixture; and measuring SERS radiation which is generated by said agent captured on the surface of said substrate and determining whether polynucleotide is present in the sample from the result of the measurement of the SERS radiation.

2. A method as claimed in claim 1, wherein the concentration of said polynucleotide is measured.

3. A method as claimed in claim 1, wherein the polynucleotide is double stranded deoxyribonucleic acid (DNA).

4. A method as claimed in claim 3, wherein the sample is one or more of the samples selected from the group consisting of a sample treated by the polymerase chain reaction (PCR), a sample treated by the Strand displacement amplification (SDA) method and a sample treated by Ligase chain reaction (LCR) method.

5. A method as claimed in claim 1, wherein the polynucleotide is ribonucleic acid (RNA).

6. A method as claimed in claim 5, wherein the sample is treated by the Qβ method with Qβ-replicas.

7. A method as claimed in claim 1, wherein the polynucleotide is single stranded DNA.

8. A method as claimed in claim 1, wherein the polynucleotide is a complex of RNA and DNA.

9. A method as claimed in claim 1, wherein said agent is one or more of the agents selected from the group consisting of 4', 6-diamidino-2-phenylindole, ethidium bromide, bisbenzimide and acridine orange.

10. A method as claimed in claim 5, wherein said agent is one or more of the agents selected from the group consisting of ethidium bromide, thiazole orange, bisbenzimide and acnridine orange.

11. A method as claimed in claim 1, wherein said substrate is one or more of the substrates selected from the group consisting of a silver colloid, a gold colloid, a copper colloid, an electrode and a metal plate.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear    (ii) MOLECULE TYPE: Other    (xi) SEQUENCE DESCRIPTION: SEQ ID NO:1:

GATGAGTTCG TGTCCGTACA ACT          23

(2) INFORMATION FOR SEQ ID NO:2:

(i) SEQUENCE CHARACTERISTICS:
      (A) LENGTH: 22 base pairs
      (B) TYPE: nucleic acid
      (C) STRANDEDNESS: single
      (D) TOPOLOGY: linear    (ii) MOLECULE TYPE: Other    (xi) SEQUENCE DESCRIPTION: SEQ ID NO:2:

CCACATCCAT ACCGGGTTTC AC          22